United States Patent
Sharma et al.

(10) Patent No.: US 10,517,299 B2
(45) Date of Patent: *Dec. 31, 2019

(54) 1-AMINO-1-CYCLOPROPANECARBOXYLIC ACID FORMULATIONS

(71) Applicant: Valent BioSciences LLC, Libertyville, IL (US)

(72) Inventors: Parvesh Sharma, Buffalo Grove, IL (US); Mitsuhiro Sasakawa, Tokyo (JP); Franklin Paul Silverman, Highland Park, IL (US); Benjamin A. Belkind, Wilmette, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/940,345

(22) Filed: Mar. 29, 2018

(65) Prior Publication Data

US 2018/0279622 A1    Oct. 4, 2018

Related U.S. Application Data

(60) Provisional application No. 62/479,540, filed on Mar. 31, 2017.

(51) Int. Cl.
*A01N 53/00* (2006.01)
*A01N 25/02* (2006.01)
*A01N 25/22* (2006.01)

(52) U.S. Cl.
CPC ............ *A01N 53/00* (2013.01); *A01N 25/02* (2013.01); *A01N 25/22* (2013.01)

(58) Field of Classification Search
CPC ........ A01N 25/02; A01N 25/22; A01N 53/00; A01N 59/06
See application file for complete search history.

(56) References Cited

U.S. PATENT DOCUMENTS

| | | | | |
|---|---|---|---|---|
| 4,367,344 A | * | 1/1983 | Gallenkamp | A01N 53/00 504/171 |
| 8,057,892 B2 | * | 11/2011 | Yang | C09J 189/00 428/323 |
| 9,040,460 B2 | | 5/2015 | Venburg et al. | |
| 9,808,004 B2 | * | 11/2017 | Venburg | A01N 37/42 |
| 2009/0011939 A1 | | 1/2009 | Thrower et al. | |
| 2010/0267557 A1 | | 10/2010 | Silverman et al. | |
| 2010/0317529 A1 | | 12/2010 | Silverman et al. | |
| 2013/0267570 A1 | | 10/2013 | Premachandran et al. | |
| 2015/0230463 A1 | * | 8/2015 | Venburg | A01N 37/42 504/144 |

OTHER PUBLICATIONS

International Search Report and Written Opinion, dated Jun. 20, 2018, in International Patent Application No. PCT/US18/25148.
Burns et al., "Ca2+ effects on ethylene, carbon dioxide and 1-aminocyclopropane-1-carboxylic acid synthase activity", Physiologia Plantarum, Apr. 1986, vol. 66, pp. 609-615.
Apelbaum et al., "Some Characteristics of the System Converting 1-Aminocyclopropane-1-carboxylic Acid to Ethylene", Plant Physiology, Jan. 1981, vol. 67, pp. 80-84.

* cited by examiner

*Primary Examiner* — Mina Haghighatian
(74) *Attorney, Agent, or Firm* — Wood, Phillips, Katz, Clark & Mortimer

(57) ABSTRACT

The present invention relates to stable 1-amino-1-cyclopropanecarboxylic acid formulations and methods of their use.

18 Claims, No Drawings

1-AMINO-1-CYCLOPROPANECARBOXYLIC ACID FORMULATIONS

FIELD OF THE INVENTION

The present invention relates to stable 1-amino-1-cyclopropanecarboxylic acid formulations and methods of their use.

BACKGROUND OF THE INVENTION 1-amino-1-cyclopropanecarboxylic acid ("ACC") is synthesized by ACC synthase in plants and acts as a precursor for the biosynthesis of ethylene. Ethylene has been shown to be involved in several plant responses including stress, fruit set, leaf abscission and anthesis. Because of its role as an ethylene precursor ACC has been used in agriculture to induce ethylene responsive events.

ACC has not been shown to be stable in solution at high concentrations. Thus, for particular agricultural uses, high concentration ACC must be stored as a solid and dissolved in a liquid solvent before application. This extra step can lead to increased cost to the end user due to the time needed to prepare the liquid compositions and possible errors made during preparation by the end user. Thus, there is a need in the art for a stable high concentration liquid ACC formulation.

SUMMARY OF THE INVENTION

The present invention is directed to stable agricultural formulations comprising 1-amino-1-cyclopropanecarboxylic acid ("ACC"), water and calcium chloride.

The present invention is further directed to a method of reducing crop load in woody perennials comprising applying a formulation of the present invention to a plant.

The present invention is further directed to a method of enhancing grape coloration comprising applying a formulation of the present invention to a plant.

DETAILED DESCRIPTION OF THE INVENTION

ACC is not stable at high concentrations in water as ACC precipitates out of solution. Surprisingly, calcium chloride when present at a specific ratio of ACC to calcium chloride prevents precipitation of ACC from water. This result was unexpected as several other salts, including known stabilizers, failed to prevent precipitation of ACC in water. See Example 1 below.

In one embodiment, the present invention is directed to stable agricultural formulations comprising ACC, water and calcium chloride, wherein the molar ratio of ACC to calcium chloride is from about 1.59:1 to about 1:2.27.

In another embodiment, the ACC is present at a concentration from about 5% to about 40% w/w or from about 5% to about 25% w/w or from 5% to about 15% w/w or from about 10% w/w to about 25% w/w.

In another embodiment, the calcium chloride is present at a concentration from about 3.5% to about 75% w/w or from about 3.5% to about 35% w/w, of from about 7% to about 75% w/w.

In another embodiment, formulations of the present invention further comprise a chelating agent, preferably, ethylenediaminetetraacetic acid ("EDTA"), preferably at a concentration from about 0.1% to about 0.2% w/w.

In a preferred embodiment, the present invention is directed to stable agricultural formulations comprising:
 about 5% to about 25% w/w ACC, preferably about 10% to about 25% w/w;
 about 3.5% to about 75% w/w calcium chloride, preferably about 7% to about 90% w/w;
 water;
 optionally, about 0.1% to about 0.2% w/w of a chelating agent; and
 optionally, about 0.25% to about 1% w/w of a preservative,
wherein the molar ratio of ACC to calcium chloride is from about 1.59:1 to about 1:2.27, preferably about 1:1.1.

In a more preferred embodiment, the present invention is directed to stable agricultural formulations comprising:
 about 10% w/w ACC;
 about 10% w/w calcium chloride;
 about 79% w/w water;
 optionally, about 0.2% w/w EDTA;
 optionally, about 0.25% w/w Kathon® CG/ICP; and
 optionally, from about 0.6% to about 0.9% w/w 2N hydrochloric acid,
wherein the formulation optionally has a pH from 2.5±0.3 to 5.3±0.3.

In another embodiment, the present invention is directed to a method of reducing crop load in woody perennials comprising applying a formulation of the present invention to a plant, preferably the woody perennial is a stone fruit tree or an apple tree and more preferably a nectarine tree, a peach tree or a plum tree.

Stone fruit trees, include but are not limited to, peach trees, nectarine trees, plum trees, apricot trees, and cherry trees.

In another embodiment, the present invention is further directed to a method of enhancing grape coloration comprising applying a formulation of the present invention to a grape plant, preferably the grape plant is *Vitus vinifera*.

Preservatives suitable for use in formulations of the present invention include, but are not limited to, Kathon® CG/ICP (5-chloro-2-methyl-1,2-isothiazol-3-one/2-methyl-2H-isothiazol-3-one; Kathon is a registered trademark of Rohm and Haas Company and Kathon CG/ICP is available from DOW Chemicals), benzoates, citric acid, ascorbic acid, parabens, potassium sorbate and combinations thereof.

Chelating agents suitable for use in formulations of the present invention include, but are not limited to, EDTA, EDTA salts, ethylene glycol-bis(β-aminoethyl ether)-N,N,N',N'-tetraacetic acid ("EGTA"), citrates, gluconates and combinations thereof.

In some embodiments, the compositions may include additional surfactants, crystal growth inhibitors, stickers, spreaders, leaf penetrants, dispersants, a systemic acquired resistance inducer, anti-foaming agents, preservatives, pH regulators, solubilization agents, a humectant, a dye, U.V. (ultra-violet) protectants, a vehicle or other components which facilitate production, storage stability, product handling application and biological efficacy.

The present invention provides very stable aqueous formulations for foliar spray, drench, in-furrow and seed treatment applications.

Throughout the application, the singular forms "a," "an," and "the" include plural reference unless the context clearly dictates otherwise.

As used herein, all numerical values relating to amounts, weight percentages and the like that are defined as "about" or "approximately" each particular value denotes plus or minus 10% of that particular value. For example, the phrase "about 10% w/w" is to be understood as encompassing values from 9% to 11% w/w. Therefore, amounts within 10% of the claimed values are encompassed by the scope of the invention.

The invention is demonstrated by the following representative examples. These examples are offered by way of illustration only and not by way of limitation.

EXAMPLES

Example 1

ACC Precipitation and Crystallization Tests

Method

Preparations of 10% w/w ACC free acid in water were found to precipitate at room temperature and/or at 5° C. To overcome this problem, salts were added individually to 10% w/w ACC aqueous solutions. These solutions were stored at room temperature and analyzed for precipitate formation. Those solutions that did not precipitate at room temperature were then incubated at 5° C. overnight and analyzed for precipitate formation the next day.

TABLE 1

Screening for Salts to Inhibit ACC Precipitation

| Salt | Precipitation (room temperature) | Precipitation (5° C.) |
|---|---|---|
| $CaCl_2$* | NO | NO |
| $MgCl_2$ | NO | YES |
| $BaCl_2$ | NO | YES |
| $Mg(NO_3)_2$ | NO | YES |
| $Ca(NO_3)_2$ | NO | YES |
| $KNO_3$ | YES | YES |
| KCl | YES | YES |
| $NH_4Cl$ | YES | YES |
| $NH_4NO_3$ | YES | YES |
| $CaSO_4$ | YES | YES |
| $Al_2(SO_4)_3$ | YES | YES |
| $(CH_3CH(OH)COO)_2Ca \cdot 5H_2O$* | YES | YES |
| Iron(III) citrate hydrate* | YES | YES |
| $AgNO_3$* | YES | YES |

*denotes salts listed as stabilizers by the Environmental Protection Agency Inert List Result As seen in Table 1, surprisingly, only calcium chloride was found to prevent precipitation at both room temperature and 5° C. This result is unexpected because other salts, including other salts known to be stabilizers, failed to prevent precipitation.

Further, formulations of ACC and calcium chloride were prepared to determine the molar ratio range at which a stable formulation occurred. These further tests demonstrated that a formulation containing a ratio of ACC to calcium chloride as high as 1.59:1 and as low as 1:2.27 prevented both precipitation of ACC at room temperature and 5° C.

Example 2

Selection of Preservatives for ACC Formulations

Method

Several preservatives were added to a formulation containing 10% w/w ACC and 10% w/w calcium chloride in water. These preservatives included Proxel™ (20% aqueous dipropylene glycol solution of 1,2-benzisothiazolin-3-one), citric acid, Kathon® CG/ICP, ascorbic acid, methyl paraben, propyl paraben, methyl paraben in combination with benzoate, propyl paraben in combination with benzoate and potassium sorbate. These formulations were then stored at both 5 and 54° C. for two weeks.

Result

Kathon® CG/ICP was found to result in the most stable formulations. Kathon® CG/ICP was then added to the formulation containing 10% w/w ACC and 10% w/w calcium chloride in water at a concentration range from 0.25% to 1% w/w. Each of these formulations were stable upon storage at both 5 and 54° C. for two weeks.

Example 3

Color Change Inhibition

Method

Formulations containing 10% w/w ACC, 10% w/w calcium chloride and Kathon® CG/ICP in water were found to undergo a color change when stored at 54° C. for two weeks. Specifically, the color changed from clear or a 1 on the Gardner Scale to a yellow color of 4-5 on the Gardener Scale. See ASTM D1544-04(2010), Standard Test Method for Color of Transparent Liquids (Gardner Color Scale), ASTM International, West Conshohocken, Pa., 2010, www.astm.org for explanation of the Gardner scale. To overcome this problem several methods were tested including lowering the pH to 4.0, packaging under nitrogen gas blanket, adding specific salts, chelating agents, antioxidants or preservatives.

TABLE 2

Screening Components to Inhibit Color Formation in ACC Formulations

| Additive | % w/w | Color (Gardner Scale) |
|---|---|---|
| None | none | 4-5 |
| Sodium citrate | 0.2 | 4-5 |
| Sodium acetate | 0.2 | 4-5 |
| Citric acid | 0.2 | 4-5 |
| Urea | 0.2 | 5-6 |
| Ascorbic acid | 0.2 | >18 |
| Fumaric acid | 0.2 | 4-5 |
| 2N hydrochloric acid | 0.6-0.9 | 3-4 |
| EDTA | 0.5 | 1-2 |
|  | 0.1 | 1-2 |
|  | 0.1 | 1-2 |

Result

As shown in Table 2, only addition of EDTA at 0.1% or 0.2% w/w resulted in a Gardner scale score of 2 or less after 2 weeks at 54° C. These formulations were further subjected to 6 additional weeks at 54° C. and maintained their clear color (i.e. Gardner Scale score of 1-2.). It was further discovered that keeping the formulations containing EDTA at 0.1% or 0.2% w/w at a pH of 4.0 provided the best results, although a pH of 5.2 maintained a clear color for at least 4 weeks at 54° C.

Example 4 pH Stability

ACC/CaCl2 Formulation of Example 4
10% w/w ACC;
10% w/w calcium chloride;
0.2% w/w EDTA;
0.25% w/w Kathon® CG/ICP; and optionally, adjusting the pH with dilute hydrochloric acid, and balance made up with water.

Method

A formula as above was prepared at various pH ranges and subjected to storage for 2 weeks at 5° C. and for 2 weeks at 54° C. Results of this study are demonstrated in Table 3, below.

Result

TABLE 3

Stability at Various pH Values

| Initial | | 2 weeks at 5° C. | | 2 weeks at 54° C. | |
|---|---|---|---|---|---|
| Assay | pH | Assay | pH | Assay | pH |
| 10.09% ACC | 4.0 | 9.97% ACC | 4.0 | 10.16% ACC | 4.0 |
| 10.1% ACC | 3.2 | 10.07% ACC | 3.0 | 10.42% ACC | 3.1 |
| 10.02% ACC | 2.7 | 10.11% ACC | 2.5 | 10.16% ACC | 2.6 |

As demonstrated in Table 3 and Example 3, above, the ACC/CaCl$_2$ formulations of the present invention remain stable at pH range from 2.7 to 5.2 under both ideal and accelerated storage conditions.

Example 5

Cotton Cotyledon Bioefficacy Assay and Cowpea Leaf Phytotoxicity Assay

Method

Aqueous solutions of ACC at 500 ppm were prepared and amended with CaCl$_2$ at 0 to 5500 ppm. The solutions were amended with 0.05% (v/v) of a non-ionic surfactant and spray applied to the adaxial surface of 10-day old cotton cotyledons using a track sprayer. In addition to ACC-containing solutions, appropriate controls were tested. Two days (48 hours) after spray application, the cotyledons from each plant were removed, weighed and incubated in sealed glass vials for 4 to 7 hours. Headspace ethylene evolution by the cotyledons was measured by gas chromatography using standard methods.

The identical spray solutions used above were foliar applied to 1) 12-day old cowpea plants using a track sprayer and 2) mid-season peach shoots. The presence of phytotoxicity (leaf burn or malformation of newly expanded leaves) was assessed at 3 and 7 days following spray application.

TABLE 4

Effect of CaCl$_2$ concentration on ethylene evolution from ACC by cotton cotyledons.

| Treatment | Molar Ratio (ACC:CaCl$_2$) | Ethylene (nL/gFW/hr*) |
|---|---|---|
| CaCl2 550 ppm | 0:1 | 1.49 |
| ACC 500 ppm | 1:0 | 39.80 |
| ACC 500 ppm + CaCl$_2$ 55 ppm | 10:1 | 33.12 |
| ACC 500 ppm + CaCl$_2$ 110 ppm | 5:1 | 53.97 |
| ACC 500 ppm + CaCl$_2$ 550 ppm | 1:1 | 54.40 |
| ACC 500 ppm + CaCl$_2$ 1100 ppm | 1:2 | 49.22 |
| ACC 500 ppm + CaCl$_2$ 5500 ppm | 1:10 | 29.38 |

*denotes nanoliters per grams fresh weight (FW) of plant per hour

Result

As seen in Table 4, application of formulas containing from a 5:1 to 1:2 molar ratio of ACC to calcium chloride to cotton cotyledons resulted in synergistic ethylene production, which is greater than that produced by 500 ppm ACC, CaCl$_2$, or the sum of both treatments. Further, application of formulas containing ACC to calcium chloride at a molar ratio of 10:1 or 1:10 resulted in less ethylene production than 500 ppm ACC alone. Thus, formulas of the present invention containing ACC and CaCl$_2$ at the specific molar ratio ranges of the present invention synergized ethylene production over the application of ACC or CaCl$_2$ alone.

No Phytotoxicity was observed as a result of any spray treatment. However, the spray treatments did eventually lead to either leaf yellowing (cowpea) or leaf abscission (peach tree shoots). However, leaf yellowing or abscission are known consequences of ethylene production and are not due to phytotoxicity of the formulations of the present invention. Thus, the ACC and calcium chloride formulations of the present invention are deemed safe on plants.

Example 6

Cotton Cotyledon Bioefficacy Assay

Method

The assay from Example 5, above, was repeated with a formulation containing 0.2% w/w EDTA.

TABLE 5

Effect of addition of EDTA to ACC formulation on ethylene evolution by cotton cotyledons.

| Treatment | Ethylene (nL/g FW/hr)* |
|---|---|
| Control | 1.0 |
| ACC 500 ppm | 27.6 |
| ACC 500 ppm + CaCl$_2$ 500 ppm | 35.6 |
| ACC 500 ppm + CaCl$_2$ 500 ppm + EDTA 10 mM | 36.2 |

*denotes nanoliters per grams fresh weight of plant per hour

Result

As seen in Table 5, application of formulas of the present invention containing EDTA did not reduce ethylene production over that seen for a 1.1:1 molar ratio of ACC to calcium chloride. Thus, formulas of the present invention containing EDTA do not negatively affect the ability to enhance ethylene production Example 7

Phytotoxicity Assay

Method

The EDTA containing formula of Example 6 was used in a phytotoxicity study as in Example 5.

Result

The EDTA containing formula of Example 6 did not cause leaf burn. Thus, the ACC and calcium chloride formulations of the present invention containing EDTA are safe on plants.

Example 8

Stone Fruit Thinning

Method

The formulation of Example 4 was diluted to prepare 300 and 600 ppm ACC solutions. These solutions were applied as a foliar spray to Zee Fire nectarine trees, Sweet Dream peach trees and Crimson Glow plum trees during full bloom.

Table 6, below, demonstrates the effect of the application of 300 or 600 ppm ACC solution of Example 8 on these stone fruit trees. Thinning activity is expressed as the number of fruit per centimeter of shoot length.
Result

TABLE 6

| Stone Fruit Thinning | | | |
|---|---|---|---|
| | Thinning Activity | | |
| | Nectarine 'Zee Fire' | Peach 'Sweet Dream' | Plum 'Crimson Glow' |
| UTC | 0.54 | 0.40 | 0.09 |
| 300 ppm ACC + 300 ppm CaCl$_2$ | 0.30 | 0.30 | 0.04 |
| 600 ppm ACC + 600 ppm CaCl$_2$ | 0.17 | 0.20 | 0.01 |

As seen in Table 6, above, ACC/CaCl$_2$ formulations of the present invention produce significant dose dependent thinning activity on stone fruit following full bloom application.

Example 9

Apple Thinning

Method

The formula from Example 8, above, was diluted to prepare 200 and 400 ppm ACC solutions. These solutions were applied as a foliar spray to Gala apple trees grown at three separate locations when the mean fruit diameter was from 18 to 20 millimeters. Table 7, below, demonstrates the effect of the application of 200 or 400 ppm ACC solution of Example 8 on these stone fruit trees. Thinning activity is expressed as the number of fruit set per 100 flower clusters after the completion of natural fruit drop.
Result

TABLE 7

| Apple Thinning | | | |
|---|---|---|---|
| | Thinning Activity | | |
| Treatment | Geneva, NY | Parkdale, OR | Monitor, WA |
| UTC | 106 | 316 | 56 |
| 200 ppm ACC | 47 | 267 | 32 |
| 400 ppm ACC | 37 | 194 | 10 |

As seen in Table 7, above, ACC/CaCl$_2$ formulations of the present invention produce as much as 80% thinning activity on apple trees following application at 18 to 20-millimeter mean fruit diameter.

Example 10

Grape Color Enhancement

Method

The formula from Example 4, above, was diluted to prepare 100, 200 and 400 ppm ACC solutions. These solutions were applied as a foliar spray to Flame Seedless table grapes grown near Fresno, Calif. at 7 days post veraison. Veraison is defined herein as the time point when 50% of the grape berries exhibit softening. Table 8, below, demonstrates the effect of the application of 100, 200 or 400 ppm ACC solution of Example 4 on these grapes. Color enhancement is expressed as the number of marketable bunches per vine.

TABLE 8

| Grape Color Enhancement | |
|---|---|
| Treatment | Marketable Bunches per Vine |
| UTC | 21 |
| 100 ppm ACC + 100 ppm CaCl$_2$ | 23 |
| 200 ppm ACC + 200 ppm CaCl$_2$ | 34 |
| 400 ppm ACC + 400 ppm CaCl$_2$ | 40 |

As seen in Table 8, above, ACC/CaCl$_2$ formulations of the present invention enhanced grape color in a dose dependent fashion and nearly doubled the number of marketable bunches per vine at 400 ppm ACC.

What is claimed is:

1. A stable agricultural formulation comprising 1-amino-1-cyclopropanecarboxylic acid (ACC), water and calcium chloride, wherein the molar ratio of ACC to calcium chloride is from about 1.59:1 to about 1:2.27.

2. The formulation of claim 1, wherein the ACC is present at a concentration from about 5% to about 25% weight by weight of the formulation.

3. The formulation of claim 2, wherein the ACC is present at a concentration from about 10% to about 25% weight by weight of the formulation.

4. The formulation of claim 1, wherein the calcium chloride is present at a concentration from about 3.5% to about 75% weight by weight of the formulation.

5. The formulation of claim 2, wherein the calcium chloride is present at a concentration from about 7% to about 75% weight by weight of the formulation.

6. The formulation of claim 1, further comprising a chelating agent.

7. The formulation of claim 6, wherein the chelating agent is present at a concentration from about 0.1% to about 0.2% weight by weight of the formulation.

8. The formulation of claim 1, further comprising a preservative.

9. The formulation of claim 8, wherein the preservative is present at a concentration from about 0.25% to about 1% weight by weight of the formulation.

10. A stable agricultural formulation comprising:
about 10% w/w ACC;
about 10% w/w calcium chloride;
about 0.2% w/w ethylenediaminetetraacetic acid; and
about 79% w/w water,
wherein w/w denotes weight by weight of the formulation.

11. The formulation of claim 10, further comprising about 0.25% w/w 5-chloro-2-methyl-1,2-isothiazol-3-one/2-methyl-2H-isothiazol-3-one.

12. The formulation of claim 10, wherein the formulation has a pH from about 4 to about 5.2.

13. A method of reducing crop load of woody perennials comprising applying a composition of claim 1 to a plant.

14. The method of claim 13, wherein the plant is a stone fruit tree.

15. The method of claim 14, wherein the stone fruit tree is selected from the group consisting of a nectarine tree, a peach tree and a plum tree.

16. The method of claim 13, wherein the plant is an apple tree.

17. A method of enhancing grape coloration comprising applying a formulation of claim 1 to a grape plant.

18. The method of claim 17, wherein the grape plant is *Vitus vinifera*.

\* \* \* \* \*